United States Patent [19]

Wovkulich et al.

[11] Patent Number: 5,200,549

[45] Date of Patent: Apr. 6, 1993

[54] ANTIPSORIATIC AGENTS

[75] Inventors: Peter M. Wovkulich, Nutley; Milan R. Uskokovic; Ann Goldstein, both of Upper Montclair, all of N.J.; John A. McLane, West Haven, Conn.

[73] Assignee: Hoffman-La Roche Inc., Nutley, N.J.

[21] Appl. No.: 764,641

[22] Filed: Sep. 24, 1991

Related U.S. Application Data

[62] Division of Ser. No. 270,980, Nov. 14, 1988, Pat. No. 5,073,568.

[51] Int. Cl.$^5$ .................. C07C 69/76; C07C 69/63
[52] U.S. Cl. ...................... 560/61; 560/227; 562/605; 562/840; 514/460; 514/550; 514/863; 514/824; 549/292
[58] Field of Search ............... 560/61, 227; 562/605, 562/840; 514/460, 550, 824, 863; 549/292

[56] References Cited

U.S. PATENT DOCUMENTS

| | | | |
|---|---|---|---|
| 4,231,938 | 11/1980 | Monaghan et al. | 549/292 |
| 4,293,496 | 10/1981 | Willard | 549/292 |
| 4,294,926 | 10/1981 | Monaghan et al. | 435/125 |
| 4,346,227 | 8/1982 | Terahara et al. | 549/292 |
| 4,444,784 | 4/1984 | Hoffman et al. | 549/292 |
| 4,450,171 | 5/1984 | Hoffman et al. | 514/460 |
| 4,582,915 | 4/1986 | Sleteinger et al. | 549/296 |
| 4,611,076 | 9/1986 | Volante et al. | 549/296 |
| 4,668,699 | 5/1987 | Hoffman et al. | 549/296 |
| 4,766,145 | 8/1988 | Lee et al. | 514/824 |
| 4,771,071 | 9/1988 | Hoffman et al. | 514/824 |
| 4,795,811 | 1/1989 | Graham et al. | 514/824 |
| 4,847,306 | 7/1989 | Lee et al. | 549/292 |
| 4,876,279 | 10/1989 | Lee et al. | 549/292 |
| 5,075,327 | 12/1991 | Tong | 514/460 |

FOREIGN PATENT DOCUMENTS

| | | |
|---|---|---|
| 254004 | 11/1987 | European Pat. Off. . |
| 349063 | 1/1990 | European Pat. Off. . |
| 59-122483 | 7/1984 | Japan . |
| 2073193 | 10/1981 | United Kingdom . |

OTHER PUBLICATIONS

Chemical Abstract: 102:78643, "Monacolin Derivatives", (1985), Abstract of JP 59-122,483.
Serizawa et al., J. Antibiot., 36(5), 604 (1983).
Serizawa et al., J. Antibiot., 36(5), 608 (1983).
Serizawa et al., J. Antibiot., 36(7), 918 (1983).
Endo, J. Med. Chem., 28(4), 401 (1985).
Yomoshita et al., J. Antibiot., 38(5), 605 (1985).
Dermatology in General Medicine, 3rd Edition, Chapter 5, pp. 49–50 and 154–159 (1987).
Molecular Cell Biology, Darnell et al. pp. 1030–1031 (1986).
J. McKenny et al., Clin. Pharm., 7(1), 21–36 (1988).
Ponec, et al., J. Cell Physiol., 133(2), 358–364 (1987).
P. 96 of Chemical & Engineering News, Aug. 1, 1988, Chemical Abstract 180 "Total Synthesis of the Angular Methyl Regioisomer of Compactin".
Drugs of Future 13(5), 475 (1988).
Dialog Databack EMBASE Abstract of Clin. Pharm., 7(1), 21 (1988).
Dialog Databack EMBASE Abstract of J. Cell. Physiol., 133(2), 358 (1987).

*Primary Examiner*—Paul J. Killos
*Attorney, Agent, or Firm*—George M. Gould; George W. Johnston; Alan P. Kass

[57] ABSTRACT

The invention relates to compounds of the formula

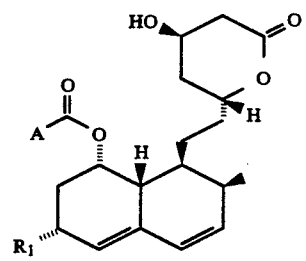

I wherein $R_1$ is hydrogen or methyl;

(Abstract continued on next page.)

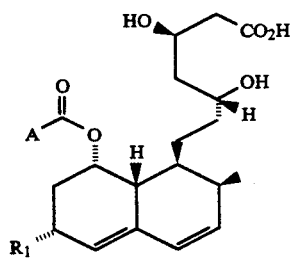

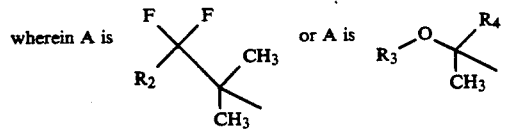

wherein A is 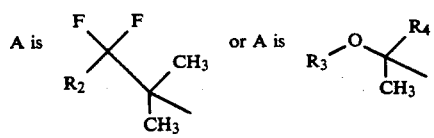

and $R_1$, $R_2$, $R_3$ and $R_4$ are as described above; or a pharmaceutically acceptable salt of said acid, a $C_{1-4}$ alkyl ester of said acid, an acetylamino-substituted-$C_{1-4}$ alkyl ester of said acid, a phenyl-dimethylamino ester of said acid or a α-monoglyceride of said acid.

The compounds of formulas I and II are useful as agents for the treatment of hyperproliferative skin diseases such as psoriasis.

wherein $R_2$ is lower alkyl; $R_3$ is phenyl, or phenyl substituted by 1 to 3 substituents selected from the group consisting of halo, lower alkyl, and lower alkoxy; and $R_4$ is hydrogen or methyl or the corresponding hydroxy acid of formula

15 Claims, No Drawings

ANTIPSORIATIC AGENTS

This is a divisional of copending application Ser. No. 07/270,980 filed on Nov. 14, 1988, now U.S. Pat. No. 5,023,568.

BRIEF SUMMARY OF THE INVENTION

The invention relates to compounds of the formula

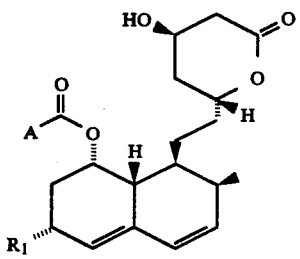

wherein $R_1$ is hydrogen or methyl;

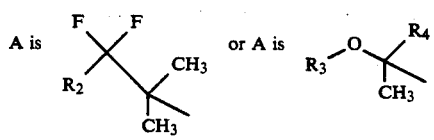

wherein $R_2$ is lower alkyl; $R_3$ is phenyl, or phenyl substituted by 1 to 3 substituents selected from the group consisting of halo, lower alkyl, and lower alkoxy; and $R_4$ is hydrogen or methyl; or the corresponding hydroxy acid of formula

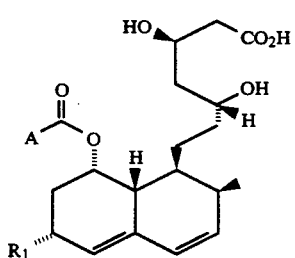

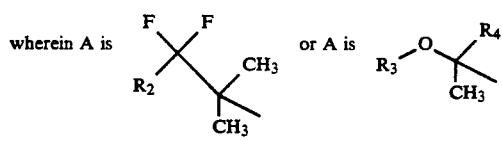

$R_1$, $R_2$, $R_3$ and $R_4$ are as described above, or a pharmaceutically acceptable salt of said acid, a $C_{1-4}$ alkyl ester of said acid, an acetylamino-substituted-$C_{1-4}$ alkyl ester of said acid, a phenyl-dimethylamino ester of said acid or a α-monoglyceride of said acid.

BACKGROUND OF THE INVENTION

Compounds known as mevinolin and mevinolin derivatives are known to inhibit the biosynthesis of cholesterol and thus are useful for their antihypercholesterolemic activity. (see U.S. Pat. No. 4,444,784 issued to Hoffman et al on Apr. 24, 1984 and U.S. Pat. No. 4,450,171 issued to Hoffman et al on May 22, 1984). The mevinolin-like compounds may be isolated from the microfungus of the genus Aspergillus as described in U.S. Pat. No. 4,231,938 issued to Monaghan et al on Nov. 4, 1980 and U.S. Pat. No. 4,294,926 issued to Monaghan et al on Oct. 13, 1981.

The most active member of this group of natural compounds in inhibiting cholesterol biosynthesis has a mevinolin structure. (see U.S. Pat. No. 4,450,171, col. 1., lines 43-51; also see U.S. Pat. Nos. 4,444,784; 4,293,496; 4,450,171; 4,582,915; 4,231,938; 4,294,926; and 4,668,699 hereby incorporated by reference.)

As antihypercholesterolemic agents, these known compounds may be administered orally or parenterally, although the oral route is generally desirable. Moreover, the known compounds have been found to be useful as anti-fungal agents which may be sprayed or dusted on plants to be protected. (see U.S. Pat. No. 4,450,171, col. 12, lines 45-66).

It has been unexpectedly found that the novel compounds of the formulas I and II are useful as agents for the treatment of hyperproliferative skin diseases. It has also been found that the compounds I and II are useful for lowering cholesterol.

DETAILED DESCRIPTION OF THE INVENTION

The invention relates to compounds of the formula

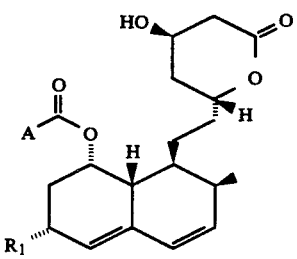

wherein $R_1$ is hydrogen or methyl;

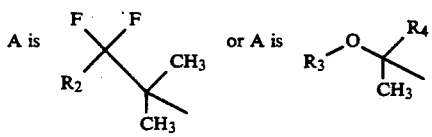

wherein $R_2$ is lower alkyl; $R_3$ is phenyl, or phenyl substituted by 1 to 3 substituents selected from the group consisting of halo, lower alkyl, and lower alkoxy; and $R_4$ is hydrogen or methyl; or the corresponding hydroxy acid of formula II

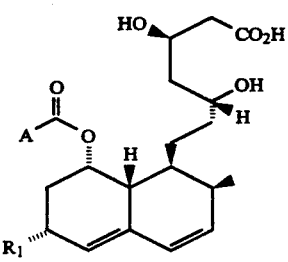

-continued wherein A is 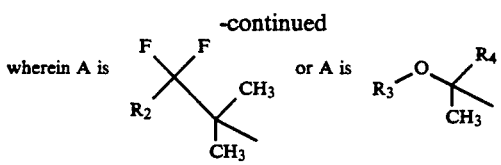

$R_1$, $R_2$, $R_3$ and $R_4$ are as described above, or a pharmaceutically acceptable salt of said acid, an alkyl ester of said acid, an acetylamino-substituted alkyl ester of said acid, a phenyl-dimethylamino ester of said acid or a α-monoglyceride of said acid.

The compounds of formulas I and II are useful in the treatment of hyperproliferative skin diseases, such as psoriasis, basal cell carcinomas, squamous cell carcinomas, keratosis, and disorders of keratinization. These compounds may be administered either orally or topically to psoriatic skin.

Compounds of formula I are converted to compounds of formula II in a manner analogous to that discussed in U.S. Pat. No. 4,444,784, as specifically described infra.

The compounds of formulas I and II are active as skin hyperproliferation antagonists, that is, as agents which inhibit the hyperproliferation of human keratinocytes. The compounds further antagonize alterations in the differentiation of keratinocytes. Accordingly, the compounds are useful as agents for the treatment of hyperproliferative skin diseases such as psoriasis, basal cell carcinomas, disorders of keratinization and keratosis.

"Normal skin" undergoes a sequence of changes resulting from changes in the proliferative basal cells to the formation of terminally differentiated corneocytes. As the epidermis differentiates in the skin, keratinocytes undergo a destructive process of terminal differentiation to produce a cellular protective layer of the stratum corneum. The process begins with the basal layer of cells proliferating and entering into the spinous layer of the skin. Within the spinous layer there is increased metabolic activity with a concomitant increase in the precursor protein for the cornified envelope and changes in the keratin expression. As the cells pass higher up the skin into the stratum corneum, enzymes responsible for crosslinking envelope proteins are active, profilaggrin processing is initiated, and higher molecular weight keratins appear. As the cell passes into the stratum corneum it is converted into a keratin filled, cornified envelope without nucleus or other organelles.

As used herein, the term "psoriasis" refers to a hyperproliferative skin disease which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer causing an increase in the basal cell cycle. Additionally, hyperkeratotic and parakeratotic cells are present.

The terms "keratosis", "basal cell carcinomas", "squamous cell carcinomas" and "disorders of keratinization" refers to hyperproliferative skin diseases in which the regulatory mechanisms for the proliferation and differentiation of skin cells are disrupted.

The term "phenyl substituted by 1 to 3 substituents" means a phenyl having one or more hydrogens replaced by a substituent.

The term "$C_{1-4}$ alkyl ester of said acid" refers to an alkyl having from 1–4 carbon atoms.

In the formulas presented herein, the various substituents are illustrated as joined to the nucleus by one of the following notations: a wedged solid line (━) indicates a substituent which is above the plane of the molecule (β-orientation) and a dashed line (⋯) or (- - -) indicates a substituent which is below the plane of the molecule (α-orientation).

As used herein the term "lower alkyl" alone or in combination denotes a straight or branched-chain saturated hydrocarbon preferably containing 1 to 6 carbon atoms, for example, methyl, ethyl, propyl, isopropyl, butyl, t-butyl pently and hexyl. The term "lower alkoxy" denotes an alkoxy containing 1 to 6 carbon atoms such as methoxy, ethoxy, propoxy, and the like. The term "halo" denotes bromo, iodo, chloro or fluoro.

The term "corresponding hydroxy acid of formula I" denotes a compound of the formula

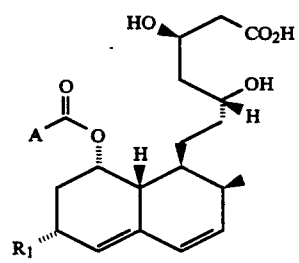

wherein A and $R_1$ are as described above.

The invention relates to compounds of formula

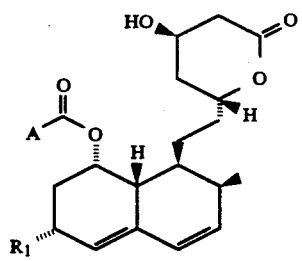

wherein $R_1$ is hydrogen or methyl;

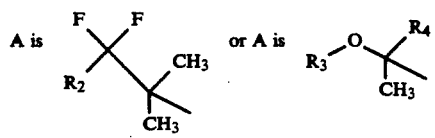

wherein $R_2$ is lower alkyl; $R_3$ is phenyl, or phenyl substituted by 1 to 3 substituents selected from the group consisting of halo, lower alkyl, and lower alkoxy; and $R_4$ is hydrogen or methyl; or the corresponding hydroxy acid of formula

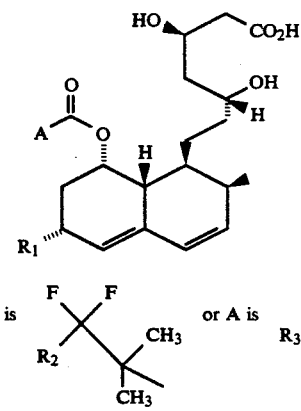

II wherein A is 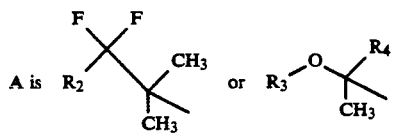

$R_1$, $R_2$, $R_3$ and $R_4$ are as described above, or a pharmaceutically acceptable salt of said acid, an alkyl ester of said acid, an acetylamino-substituted alkyl ester of said acid, a phenyl-dimethylamino ester of said acid or a α-monoglyceride of said acid.

The invention also relates to processes for making the compounds of formulas I and II and to a method for treating hyperproliferative skin diseases such as psoriasis which comprises the oral and/or topical administration of effective amounts of the compounds of formulas I or II.

The compounds of formula I and the corresponding hydroxy acids II thereof are also useful as agents for lowering cholesterol.

In accordance with the invention, compounds of formula I wherein $R_1$ is hydrogen or methyl; and A is wherein $R_2$ is lower alkyl; $R_3$ is phenyl, or phenyl substituted by 1 to 3 substituents selected from the group consisting of halo, lower alkyl, and lower alkoxy; and $R_4$ is hydrogen or methyl may be prepared as hereinafter described in Reaction Scheme I.

REACTION SCHEME I

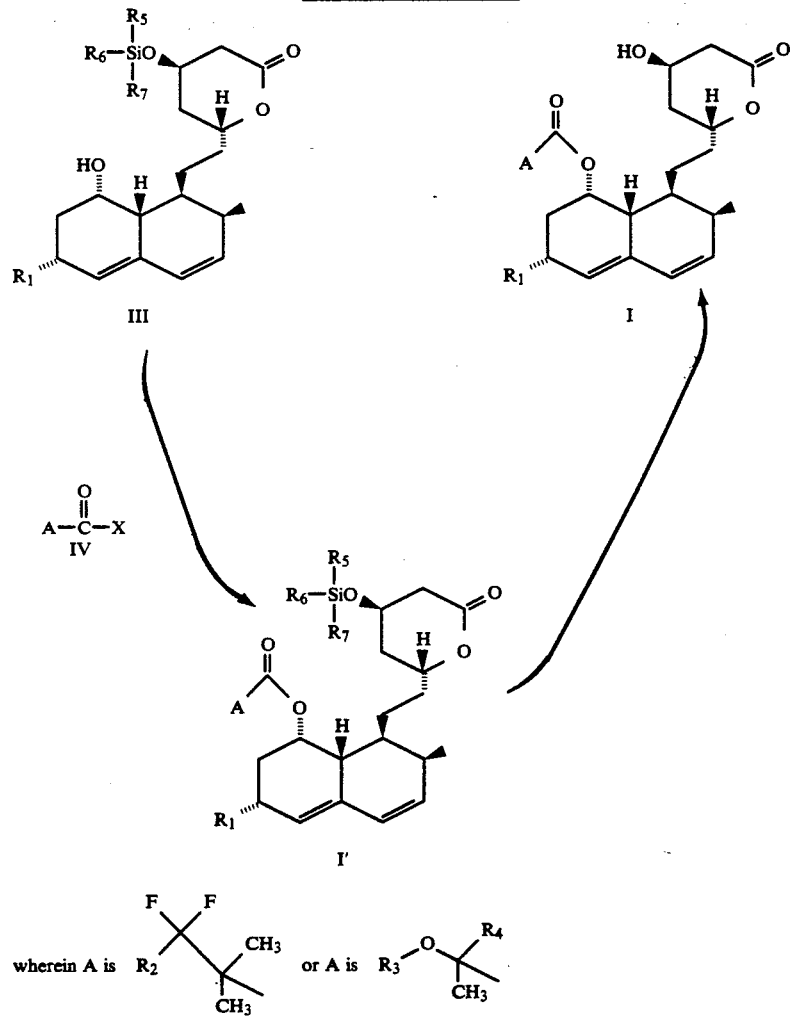

wherein $R_1$ is hydrogen or methyl; $R_2$ is lower alkyl; $R_3$ is phenyl or phenyl substituted by 1 to 3 substituents selected from the group consisting of halo, lower alkyl, and lower alkoxy; X is chloro or bromo; $R_4$ is hydrogen or methyl; and $R_5$, $R_6$ and $R_7$ are independently lower alkyl, or phenyl provided that no more than two of $R_5$, $R_6$ and $R_7$ are phenyl.

In Reaction Scheme I, a compound of the formula

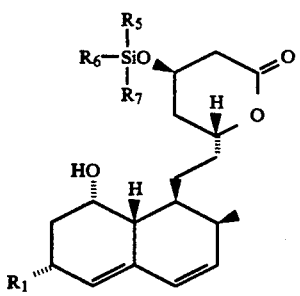   III wherein $R_5$, $R_6$, and $R_7$ are independently lower alkyl or phenyl provided that no more than two of $R_5$, $R_6$ and $R_7$ are phenyl, is known or can be prepared in accordance with known methods such as those set forth in U.S. Pat. No. 4,444,784.

A compound of formula

   IV wherein A is

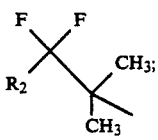

X is chloro or bromo; and $R_2$ is lower alkyl is new and is prepared as described below. Compound IV is reacted with a compound of formula III in an organic solvent such as tetrahydrofuran, dichloromethane, $CH_3CN$, or more preferably pyridine, in the presence of a base such as triethylamine, imidazole, 4-N,N-dimethylaminopyridine, or more preferably 4-pyrrolidinopyridine, at about room temperature to about reflux temperature of the solvent, or preferably at about 50° C.

After conventional work-up a compound of formula

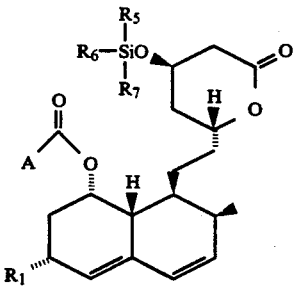   I' wherein A, $R_5$ $R_6$ and $R_7$ are as described above is obtained.

The compound of formula I is reacted with a silyl ether cleaving reagent such as dilute aqueous hydrofluoric acid; or more preferably, aqueous tetrabutylammonium fluoride buffered with an acid such as trifluoroacetic acid, acetic acid, or a mineral acid like hydrochloric acid, in a solvent such as methanol, ethanol or dioxane, or more preferably tetrahydrofuran. Upon conventional work-up there is obtained a compound of formula

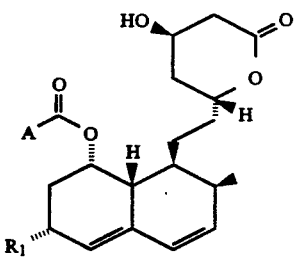   I wherein $R_1$ is hydrogen or methyl; A is

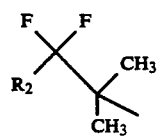

and $R_2$ is lower alkyl.

Compounds of formula I can be hydrolyzed with bases such as NaOH to yield the corresponding salts such as sodium salts. Careful acidification of the salts yields the corresponding hydroxy acid form of formula II. Compounds of formula II can conversely be converted to compounds of formula I at acidic pH.

Furthermore, compounds of formula I may be treated under acidic or basic catalysis with methanol, ethanol, propanol or butanol or with phenyl-, dimethylamino-, or acetylaminoalkanols to yield the corresponding esters of the hydroxy acid compounds of formula II.

Analogously, as shown in Reaction Scheme I, compounds of formula I

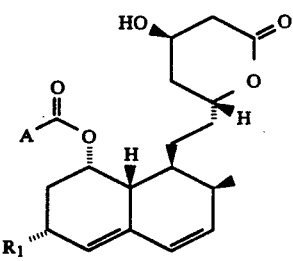   I wherein A is

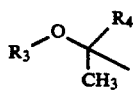

and $R_3$ is phenyl or phenyl substituted by 1 to 3 substituents selected from the group consisting of halo, lower alkyl and lower alkoxy, and $R_4$ is hydrogen or methyl, may be prepared by the reaction of a compound of formula III with a compound of formula

   IV wherein A is

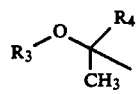

and $R_3$, $R_4$ and X are as described above. Compound III is preferably reacted with the acid chloride of Compound IV, 2-(4-chlorophenoxy)-2-methylpropionyl chloride, in the presence of an organic base, preferably pyridine or 4-N,N-dimethylaminopyridine, and extracted with an organic solvent such as a dry ether solvent, such as dialkyl ether or preferably diethyl ether to obtain the compound of the formula

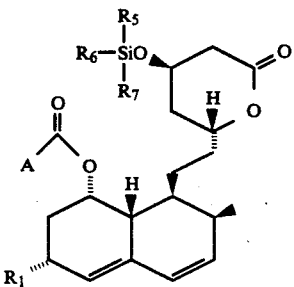   I' which may be isolated by conventional means.

The compound of formula I' is reacted with acetic acid and tetrabutylammonium fluoride in tetrahydrofuran to obtain a mixture which is taken up in an organic solvent such as a dry ether solvent, like dipropyl ether or more preferably diethyl ether to obtain the compound of formula

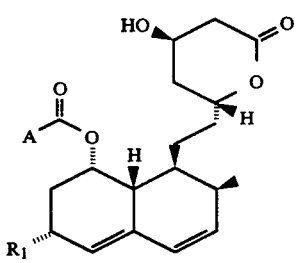   I which may be isolated by conventional means.

Preferred compounds of formula I are:

2-(4-chlorophenoxy-2-methylpropionic acid [1S-[1α,-3α,7β,8β(2R*,4R*),8aβ]]-1,2,3,7,8,8a-hexahydro-3,7-dimethyl-8-[2-[tetrahydro-4-hydroxy-6-oxo-2H-pyran-2-yl]ethyl]-1-naphthalenyl ester.

3,3-difluoro-2,2-dimethylbutanoic acid, [1S-[1α,3α,-7β,8β(2R*,4R*)8aβ]]-8-[2[tetrahydro-4-hydroxy-6-oxo-2H-pyran-2-yl]ethyl]-1,2,3,7,8,8a-hexahydro-3,7-dimethyl-1-naphthalenyl ester.

The compounds of formula IV wherein A is

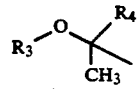

are known or can be prepared in accordance with known methods, such as reacting the corresponding carboxylic acid with an acid halide forming reagent such as thionyl chloride, thionyl bromide or oxalyl chloride, in a conventional solvent for such reactions, like dichloromethane.

Exemplary of compounds of formula IV are:
2-(4-chlorophenoxy)-2-methylpropionyl chloride,
2-(3-chlorophenoxy)-2-methylpropionyl chloride,
2-(2-chlorophenoxy)-2-methylpropionyl chloride,
2-(4-chlorophenoxy)-2-methylpropionyl bromide,
2-(4-methoxyphenoxy)-2-methylpropionyl chloride,
2-(4-ethoxyphenoxy)-2-methylpropionyl chloride,
2-(3-methoxyphenoxy)-2-methylpropionyl bromide,
2-(2-methoxyphenoxy)-2-methylpropionyl bromide; and
2-(2-ethoxyphenoxy)-2-methylpropionyl chloride.

Compounds of formula

   IV wherein A is

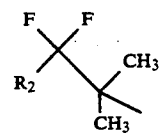

are novel and are an aspect of this invention as are the corresponding carboxylic acids of formula

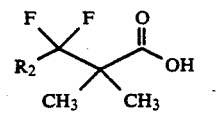   IV' which are also an aspect of this invention.

REACTION SCHEME II

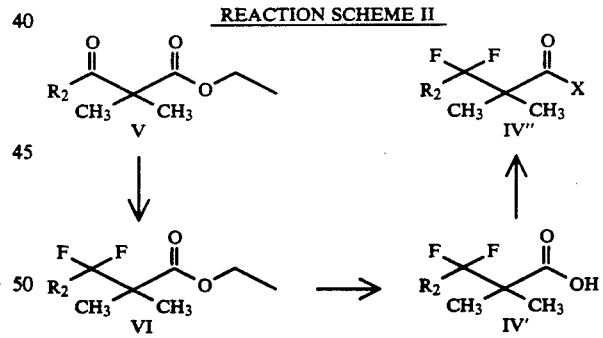

As shown in Reaction Scheme II compounds of formula IV are prepared as follows. Compounds of formula

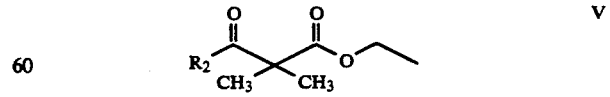   V wherein $R_2$ is lower alkyl are known or can be prepared in accordance with known methods.

A compound of formula V is reacted with a selective fluorinating agent such as sulfur tetrafluoride or diethylamino sulfur trifluoride to obtain a compound of formula

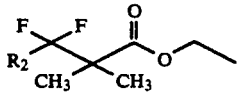

VI

A compound of formula VI is treated with an ester cleaving reagent such as an aqueous mineral acid like hydrochloric acid, or sulfuric acid, or an aqueous base such as lithium, potassium hydroxide, or, more preferably aqueous sodium hydroxide, an organic solvent such as tetrahydrofuran, ethanol, or more preferably without an organic solvent to obtain upon conventional work-up a compound of formula

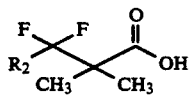

IV'

A compound of formula IV' is converted to a compound of formula IV" with acid halide forming reagents as described above.

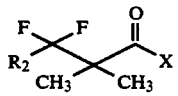

IV"

Exemplary of compounds of formula IV wherein A is

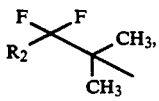

are
3,3-difluoro-2,2-dimethyl butanoic acid;
3,3-difluoro,-2,2-dimethyl pentanoic acid; and
3,3-difluoro-2,2-dimethyl hexanoic acid.

Effect of Compounds of Formulas I and II on the Proliferation of Cultured Human Keratinocytes The compounds of formulas I and II as described above can be administered orally, for the treatment of hyperproliferative skin diseases such as psoriasis, basal cell carcinomas, disorders of keratinization and keratosis to warm-blooded animals which need such treatment. More specifically, the compounds of formula I as described above can be administered orally to the adult human in dosages that are in the range of about 10 to about 80 mg per day for the treatment of hyperproliferative skin diseases such as psoriasis, basal cell carcinomas, squamous cell carcinomas disorders of keratinization and keratosis.

The compounds of formulas I and II can be administered topically, for treatment of hyperproliferative skin diseases, such as psoriasis, basal cell carcinomas, squamous cell carcinomas, disorders of keratinization and keratosis to warm-blooded animals which need such treatment. More specifically, the compounds of formula I as described above can be administered topically in dosages that are in about 1 to about 200 micrograms per gram of topical formulation per day for the treatment of such diseases, preferably about 1 to about 50 micrograms per gram of topical formulation per day are administered to a patient.

The useful activity of compounds of formula I as agents for the treatment of hyperproliferative skin diseases are demonstrated by the following test procedures.

MATERIALS & METHODS

1. Culture Conditions

Human neonatal foreskins were collected by circumcision and placed into tubes containing DMEM media. Upon arrival at the laboratory the foreskins were mechanically trimmed of excess dermis and treated with a solution of trypsin/EDTA (0.05%/0.02%) at 4° C. overnight. The epidermis was stripped from the dermis, agitated in buffered saline to remove basal keratinocytes and to separate the stratum corneum which was subsequently removed. The separated cells were centrifuged, resuspended in media, counted and the keratinocytes were plated onto a plain plastic culture dish.

The keratinocytes were plated at a density of about $10^5$ cells/cm$^2$ in 35 cm$^2$ dishes. The cells were grown in keratinocyte growth media (KGM ®-modified MCDB 153 containing antibiotics by Clonetics of Boulder, Colo.) according to protocols originally developed by Boyce, S. T. and Ham, R. G., *J. of Tissue Culture Meth.* 9:83–93 (1985). The cells were grown for 5–10 days and changed every 2–3 days with keratinocyte growth media containing 1.5 mM CaCl$_2$ (hereinafter KGM ®/1.5 mM CaCl$_2$) until cells reached a 75% confluency by visual observation. All the cultures were incubated in a humidified atmosphere of 5% CO$_2$ at 37° C.

To establish keratinocyte cell cultures as antiproliferative assays, cells prepared as described in the foregoing were washed with PBS and removed from the culture surface with a solution of trypsin/EDTA (0.25%/0.03%). The removed cells were then centrifuged, resuspended in the KGM ®/1.5 mM CaCl$_2$ and counted. The cells were then distributed to 6 well plates at 100,000 cells per well as described in the foregoing. Each well had an area of 9.5 cm$^2$. After 24–48 hours KGM ®/1.5 mM CaCl$_2$ which contained test compounds was added to the cells. The cultures maintained for seven days. The media was changed every 2–3 days.

2. Test Solutions

Solutions of the test compounds were prepared as follows: 1 milligram quantities were received in amber glass vials, and stored at −20° C. Sufficient 100% ethanol was added directly to vials to obtain a millimolar solution that was subsequently aliquoted into small amber vials, overlayed with argon gas and stored at −20° C. Each stock solution was thawed once, used and discarded. Aliquots from the stock solutions were diluted directly into medium and then serially diluted from micromolar to 10$^{-12}$M concentrations. Dilutions from 10$^{-7}$M to 10$^{-12}$M had ethanol added for a final concentration of 0.1%. Stock solutions were used within one month. Control cultures were treated with 0.1% ethanol.

3. Cell Proliferation

For each experiment every culture well received the same number of cells from the same culture source. At the termination of the experiment the number of cells per was determined by the following procedure. Wells were washed twice with PBS and then incubated for approximately 10–20 minutes at 37° C. with a trypsin- /EDTA solution (0.25%/03%). PBS plus 0.1% soybean trypsin inhibitor was added and the cells were suspended. An aliquot of the cells was placed into isotonic buffered saline and counted on an electronic particle counter (e.g. Coulter Counter ® device by Coulter Electronics of Hialeah, Fla.).

Quantification of proliferation was done by enumerating the number of keratinocyte cells in each well using the Coulter Counter ®. Results shown in Table 1 below show the percent reduction of keratinocyte cell number calculated for each of 4 concentrations of test compounds tested according to the formula:

$$\left[100 - \left(\frac{\text{mean number of cells in experimental cultures}}{\text{mean number of cells in control cultures}}\right)\right] \times 100$$

For statistical analysis, the mean was calculated for all wells in each treatment group. Standard error was determined by nonbiased analysis using a value for the number of wells in each group, preferably N=3.

TABLE 1

INHIBITION OF TEST COMPOUNDS ON KERATINOCYTE PROLIFERATION

| Compound | Dosage of Compound (M) | Percent Inhibition on Keratinocyte Proliferation | Standard Deviation |
|---|---|---|---|
| 1. ETOH Control | | 0.00 | 24.48 |
| 2. A | $10^{-10}$ | 20.92 | 40.81 |
| | $10^{-8}$ | 6.28 | 24.83 |
| | $10^{-7}$ | 15.23 | 27.09 |
| | $10^{-6}$ | 49.71 | 23.69 |
| 3. B | $10^{-10}$ | 17.97 | 24.57 |
| | $10^{-8}$ | 14.61 | 24.12 |
| | $10^{-7}$ | 31.23 | 23.81 |
| | $10^{-6}$ | 95.80 | 29.03 |

In Table 1, A is 2-(4-chlorophenoxy-2-methylpropionic acid [1S-[1α,3α,7β,8β(2R*,4R ),8aβ]]-1,2,3,7,8,8a-hexahydro-3,7-dimethyl-8-[2-[tetrahydro-4-hydroxy-6-oxo-2H-pyran-2-yl]ethyl]-1-naphthalenyl ester.

In Table 1, B is 3,3-difluoro-2,2-dimethylbutanoic acid, [1S-[1α,3α,7β,8β(2R*,4R*)8aβ]]-8-[2[tetrahydro-4-hydroxy-6-oxo-2H-pyran-2-yl]ethyl]-1,2,3,7,8,8a-hexahydro-3,7-dimethyl-1-naphthalenyl ester.

Each compound was tested in triplicate. The control (ETOH), as noted above, was 0.1% ethanol.

CONCLUSION

The foregoing results evidence that at a test compound dosage of $10^{-6}$ inhibition of keratinocytes cells is the greatest. Of the experiments conducted for each of the test compounds, it was observed that at a concentration of $10^{-6}$M, each of the compounds of formula I inhibited about 50% of the proliferation of the keratinocyte cells. Compound B was found to inhibit more of the cells than compound A at a $10^{-6}$M concentration (i.e. 95.80%).

These data indicate that each of the compounds of formula I tested restrained the proliferation of human keratinocyte cells in vitro, without toxicity to the cells. From these results it can be seen that each of the tested compounds is useful as an agent in the treatment of hyperproliferative skin diseases such as psoriasis.

As discussed above, mevinolin and mevinolin derivatives as well as the corresponding hydroxy acids of such compounds are known to be useful as cholesterol lowering agents.

In the present invention it has been found that compounds of formula I exhibit cholesterol lowering activity, as well as being useful in the treatment of hyperproliferative skin diseases.

Oral dosage forms comprising compounds of formulas I or II of the invention may be incorporated in capsules, tablets and the like with pharmaceutically acceptable carrier materials.

The useful activity of compounds of formulas I or II as agents for lowering cholesterol is demonstrated by the following test procedures.

INHIBITION OF CHOLESTEROL BIOSYNTHESIS

Materials and Methods

HepG2 cells are maintained in 175 cm² T flasks in Darlington Medium supplemented with 10% fetal bovine serum (FBS). Darlington Medium consists of 3 parts Minimal Essential Medium, 1 part Waymouth's MAB87/3 medium and $3 \times 10^{-8}$M sodium selenite. This medium is supplemented with 100 U/ml penicillin, 100 ug/ml streptomycin and 2.5 ug/ml Fungizone. In order to establish optimal conditions for the whole cell cholesterol biosynthesis assay, preliminary experiments were performed. 0.25, 0.5, 0.75 or $1 \times 10^6$ cells were seeded into 6 well cluster plates in 2 ml of fully supplemented Darlington Medium. The serum supplemented medium was aspirated after 72 hours and replaced with serum free Darlington Medium with antibiotics. After 24, 48 or 72 hours serum free, the cells received either 0.5 or 1 mCi ³H₂O/ml medium. This medium was aspirated after 24 hours and the cells were washed twice with phosphate buffered saline. The cells were frozen overnight at $-20°$ C. after which they were harvested from the wells with 1 ml of trypsin-EDTA. Extracted lipids were separated on an HPLC system; cholesterol peaks were collected and counted in a scintillation counter. Results are expressed as the dpm ³H₂O incorporated into cholesterol.

In the screening assay the cells received compounds at various concentrations concommitantly with ³H₂O. When ethanol was the vehicle, the final ethanol concentration was 0.5%, and control wells with that concentration of ethanol were used in each experiment. Results are expressed as the percent dpm ³H₂O incorporated into cholesterol in treated vs control wells. $IC_{50}$ values are calculated using a linear regression analysis.

TABLE 2

Summary of $IC_{50}$ Data (μmolar)
Inhibition of Cholesterol Biosynthesis in HepG2 Cells

| Test | mevinolin | B | A |
|---|---|---|---|
| I | 0.020 | — | 0.030 |
| II | 0.100 | — | 0.500 |
| III | 0.076 | — | 0.101 |
| IV | 0.008 | 0.005 | — |

As can be seen in above Table 2, the inhibition of cholesterol biosynthesis of compound A of the invention, as compared to mevinolin, was determined in tests I through III.

The inhibition of cholesterol biosynthesis of compound B of the invention, as compared to mevinolin, was determined in test IV.

CONCLUSIONS

Both compounds A and B of the invention show activity as cholesterol biosynthesis inhibitors in this test.

Illustrative of the pharmaceutically acceptable carrier materials which may be incorporated into capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising compounds of formula I of the invention include: ointments and creams encompassing formulations having oleaginous, adsorbable, water-soluble and emulsion-type bases such as petroleum, lanolin, polyethylene glycols and the like.

Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like.

Gels are semi-solid preparations made by gelling a solution or suspension of the active ingredient in a carrier vehicle. The vehicles, which can be hydrous or anhydrous, are gelled using a gelling agent, such as carboxy polymethylene, and neutralized to a proper gel consistency with the use of alkalies, such as, sodium hydroxide and amines, such as, polyethylenecocoamine.

As used herein, the term "topical" denotes the use of the active ingredient, incorporated in a suitable pharmaceutical carrier, and applied at the site of inflammation for the exertion of local action. Accordingly, the topical compositions include those pharmaceutical forms in which the compound is applied externally by direct contract with the skin. The topical dosage forms comprise gels, creams, lotions, ointments, powders, aerosols and other conventional forms for applying medications to the skin obtained by admixing the compounds of formula I with known pharmaceutical topical carrier materials. In addition to the application to the skin, the topical compositions of this invention can also be employed in the treatment of inflammations of mucous membranes, where such membranes are accessible to topical application of medication. For example, the topical composition can be applied to the mucous lining of the mouth or lower colon.

The Examples which follow further illustrate the invention. All temperatures are in degrees Celsius unless otherwise stated.

EXAMPLE 1

Preparation of 2-(4-chlorophenoxy)-2-methylpropionic acid [1S-[1α,3α,7β,8β(2R*, 4R*),8aβ]]-1,2,3,7,8,8a-hexahydro-3,7-dimethyl-8-[2-[tetrahydro-4-hydroxy-6-oxo-2H-pyran-2-yl]ethyl]-1-naphthalenyl ester A mixture of (1S-(1α(4R*,6R*),2α,6β,8β,8aα]]-4-[[(1,1-dimethylethyl)dimethylsilyl]oxy]-6-[2-(1,2,6,7,8,8a-hexahydro-8-hydroxy-2,6-dimethyl-1-naphthalenyl)ethyl]tetrahydro-2H-pyran-2-one in an amount of 1.00 g (2.29 mmol), 18.6 ml of dry pyridine, 1.40 g (1.15 mmol) 4-N,N-dimethylaminopyridine and 5.34 g (22.9 mmol) of 2-(4-chlorophenoxy)-2-methylpropionyl chloride was heated at 50° C. for 6¾ hour, then stirred overnight at room temperature. Ice chips were then added, and after 30 min the mixture was poured into ice water and extracted four times with diethylether. The combined ether layers were washed with water, then washed with 0.1M $H_2SO_4$ and then dried over a conventional drying agent, preferably anhydrous sodium sulfate. The mixture was filtered and volatiles removed under reduced pressure (i.e. below atmospheric pressure, preferably around 30 mm). The residue was dissolved in diethylether, washed with saturated sodium bicarbonate solution and dried over anhydrous sodium sulfate. The mixture was filtered and volatiles removed under reduced pressure to leave 1.6 of 2-(4-chlorophenoxy)-2-methylpropionic acid-[1S-[1α,3α,7β,8β(2R*,4R*),8aβ]]-8-[2[tetrahydro-4-[[(1,1-dimethylethyl)dimethylsilyl]oxy]-6-oxo-2H-pyran-2-yl]ethyl]-1,2,3,7,8,8a-hexahydro-3,7-dimethyl-1-naphthalenyl ester as a brown oil which was used directly without further purification.

The crude product obtained above was stirred with 5.6 ml of tetrahydrofuran, 0.291 ml of water, 0.402 ml of acetic acid and 5.22 ml of a 1.0M solution of tetrabutylammonium fluoride in tetrahydrofuran for 23 hours. The mixture was taken up in diethylether washed with brine, dried over anhydrous sodium sulfate, filtered and volatiles removed under reduced pressure. The residue was filtered through silica gel to give, after evaporation of volatiles under reduced pressure, 0.91 of 2-(4-chlorophenoxy)-2-methylpropionic acid [1S-[1α,-3α,7β,8β(2R*, 4R*),8aβ]]-1,2,3,7,8,8a-hexahydro-3,7-dimethyl-8-[2-[tetrahydro-4-hydroxy-6-oxo-2H-pyran-2-yl]ethyl]-1-naphthalenyl ester. This compound was chromatographed by conventional means on silica gel eluting with hexane/ethyl acetate (15:85) to give 0.376 g of 2-(4-chlorophenoxy)-2-methylpropionic acid [1S-[1α,3α,7β,8β(2R*,4R*),8aβ]]-1,2,3,7,8,8a-hexahydro-3,7-dimethyl-8-[2-[tetrahydro-4-hydroxy-6-oxo-2H-pyran-2-yl]-ethyl]-1-naphthalenyl ester, which on precipitation from hexane/1-chlorobutane gave an amorphous solid with a m.p. of 65° C. [$\alpha^{25}$ = +226.1 ($CHCl_3$, C, 0.52). Significant nmr data ($cDCl_3$, 200 mHz) d 7.16 (d, J=9$H_z$, 2H), 6.87 (d, J=9$H_z$, 2H), 5.98 (d, J=10 Hz, 1H), 5.68 (dd, J=6, 10 Hz, 1H), 5.50 (brs, 2H), 4.55 (m, 1H), 4.36 (nm, 1H), 2.72 (dd, J=5, 18 Hz, 1H), 2.59 (dd, J=4, 18 Hz, 1H), 1.53 (s,6H), 1.00 (d, J=7$H_2$, 3H), 0.88 (d, J=7 Hz, 3H). Calc $C_{29}H_{37}ClO_6$: C 67.37, H 7.21, found: C 67.02, H 7.48.

EXAMPLE 2

Preparation of 3,3-difluoro-2,2-dimethylbutanoic acid. [1S-[1α,3α,7β,8β(2R*,4R*)8aβ]]-8-[2[tetrahydro-4-[[(1,1-dimethylethyl)dimethylsilyl]oxy]-6-oxo-2H-pyran-2-yl]ethyl]-1,2,3,7,8,8a-hexahydro-3,7-dimethyl-1-naphthalenyl ester To 1.55 g (9.86 mmol) 3,3-difluoro-2,2-dimethylbutanoic acid in 5 ml of dry dichloromethane was added 3.45 ml (39.5 mmol) of oxalyl chloride. The mixture was stirred at room temperature for 20 hours then solvent and excess reagent removed by distillation followed by addition of carbon tetrachloride and distillation of the solvent. The cooled 3,3-difluoro-2,2-dimethylbutanoyl chloride thus formed was dissolved in 8 ml of dry pyridine and added to a mixture of 2.15 g (4.93 mmol) of [1S-[1α(4R*,6R*),2α, 6β,8β,8aα]]-4-[[(1,1-dimethylethyl)dimethylsilyl]oxy-[2-(1,2,6,7,8,8a-hexahydro-8-hydroxy-2,6-dimethyl-1-naphthalenyl)ethyl]tetrahydro-2H-pyran-2-one, 0.35 g of 4-pyrrolidinopyridine and 10 ml of dry pyridine. The mixture was heated at 50° overnight then cooled and quenched by the addition of ice chips. The mixture was taken up in diethyl ether and washed successively with water, dilute sulfuric acid and saturated sodium bicarbonate. The mixture was dried over anhydrous sodium sulfate, filtered and concentrated under reduced pressure. The residue was chromatographed on silica gel eluting with hexane/dichloromethane/ethyl acetate (25:25:50) to give 0.314 g of 3,3-difluoro-2,2-dimethylbutanoic acid, [1S-[1α,3α,7β,8β(2R*,4R*)8aβ]]-8-[2[tetrahydro-4-[[(1,1-dimethylethyl)dimethylsilyl]oxy]-6-oxo-2H-pyran-2-yl]ethyl]-1,2,3,7,8,8a-hexahydro-3,7-dimethyl-1-naphthalenyl ester.

EXAMPLE 3

Preparation of 3,3-difluoro-2,2-dimethylbutanoic acid, [1S-[1α,3α,7β,8β(2R*,4R*)8aβ]]-8-[2-[tetrahydro-4-hydroxy-6-oxo-2H-pyran-2-yl]ethyl]-1,2,3,7,8,8a-hexahydro-3,7-dimethyl-1-naphthalenyl ester A mixture of 0.46 g (0.81 mmol) of 3,3-difluoro-2,2-dimethylbutanoic acid, [1S-[1α,3α,7β,8β(2R*,4R*)8aβ]]-8-[2[tetrahydro-4-[[(1,1-dimethylethyl)dimethylsilyl]oxy]-6-oxo-2H-pyran-2-yl]ethyl]-1,2,3,7,8,8a-hexahydro-3,7-dimethyl-1-naphthalenyl ester, 2 ml of tetrahydrofuran, 0.463 ml of acetic acid, 0.103 ml of water and 1.85 ml of 1.0M solution of tetrabutylammonium fluoride was stirred at room temperature for 32 hours. The mixture was taken up in diethyl ether and the ether extract washed successively with water, then brine, then dried over anhydrous sodium sulfate. The mixture was filtered and concentrated under reduced pressure. Chromatography of the residue on silica gel eluting with hexane/ethyl acetate (1:1) gave 0.329 g 3,3-difluoro-2,2-dimethylbutanoic acid, [1S-[1α,3α,7β,8β-(2R*,4R*)8aβ]]-8-[2-[tetrahydro-4-hydroxy-6-oxo-2H-pyran-2-yl]ethyl]-1,2,3,7,8,8a-hexahydro-3,7-dimethyl-1-naphthalenyl ester The analytical sample was crystallized from chlorobutane. mp 154–159° C. Calc for $C_{25}H_{36}O_5F_2$: C 66.06, H 7.98; found: C 65.93, H 8.13, significant nmr data (CDCl$_3$, 200 mHz) δ 5.98 (d, J=10 Hz,1H) 5.79 (dd, J=6,10 Hz,1H), 5.51 (brs, 1H), 5.38 (nm, 1H), 4.58 (m, 1H), 4.36 (nm, 1H), 1.72 (t, J=20 Hz,3H), 1.05 (d, J=7 Hz,3H), 0.85 (d, J=7 Hz, 3H).

EXAMPLE 4

Preparation of 3,3-difluoro-2,2-dimethylbutanoic acid

A mixture of 12.25 g (77.5 mmol) 2,2-dimethyl-3-oxobutanoic acid ethyl ester, and 25 g (155.1 mmol) diethylaminosulfurtrifluoride was heated for 55 hour, then cooled. Dichloromethane was added and the mixture was poured onto ice. The dichloromethane layer was washed successively with water, saturated sodium bicarbonate solution and brine, then dried over anhydrous sodium sulfate. The mixture was filtered, then concentrated under reduced pressure to give 24.6 of a mixture which contained 3,3-difluoro-2,2-dimethylbutanoic acid ethyl ester. This material was heated to reflux with 304 ml of 1M sodium hydroxide solution for 3¾ hour then cooled.

The mixture was extracted with dichloromethane. The dichloromethane extract was washed with water, dried over anhydrous sodium sulfate, filtered and concentrated under reduced pressure. This residue was refluxed with 81 ml of 1M sodium hydroxide solution for 3¾ hour, cooled, and extracted with dichloromethane. The combined aqueous layers from the above were acidified to about pH2 with dilute sulfuric acid and extracted with dichloromethane. This extract was washed with brine, dried over anhydrous sodium sulfate, filtered and concentrated under reduced pressure. The residue was further purified by bulb to bulb transfer at 35–40 mm Hg with a heating bath at 90°–120° C., to give 6.0 g of solid 3,3-difluoro-2,2-dimethylbutanoic acid. The product was further purified by crystallization from dichloromethane/pentane to give 3.0 of 3,3-difluoro-2,2-dimethylbutanoic acid, significant nmr data (CDCl$_3$ 200 mHz) 1.73 (t, J=18 Hz, 3H), 1.38 (S, 3H).

EXAMPLE 5

Oral dosage formulation for Compounds of Formula I or the corresponding hydroxy acid of compound II thereof

| | |
|---|---|
| 1. Compound of Formula I or II | 20 milligrams |
| 2. Lactose hydrose | 150 milligrams |
| 3. Starch 1500 | 30 milligrams |
| 4. Talc | 20 milligrams |

MANUFACTURING PROCESS

A. Mix 1 with a portion of 2.
B. Add 3 and 4, and mix.
C. Add the remainder of 2, mix thoroughly, and pass through a suitable mill. Capsules are filled with the composition thus prepared.

EXAMPLE 6

Preferred Formulation for Topical Dosage of Compounds of Formula I or II.

| | |
|---|---|
| 1. Compound of Formula I or II | 10.0 micrograms |
| 2. Stearyl alcohol | 4.0 g |
| 3. Cetyl alcohol | 4.0 g |
| 4. Mineral oil | 3.0 g |
| 5. Polysorbate 60 | 4.5 g |
| 6. Sorbitan stearate | 4.5 g |
| 7. Propylene glycol | 10.0 g |
| 8. Methyl paraben | 0.18 g |
| 9. Propyl paraben | |
| 10. Water | q.s. to 100.00 g |

MANUFACTURING PROCESS

A. Heat 2 through 6 to 80° C., which melts all ingredients (oil phase).
B. Dissolve 1 in oil phase.
C. Heat 7 and 10 to 90° C. (aqueous phase).
D. Dissolve 8 and 9 in aqueous phase.
E. Add aqueous phase to oil phase, and stir rapidly to form an emulsion.
F. Cool slowly to 50° C. to allow the emulsion to congeal.
G. Continue stirring slowly until the emulsion cools to room temperature.

We claim:

1. A compound of the formula

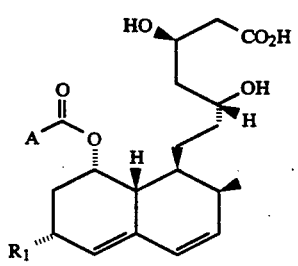

II wherein $R_1$ is hydrogen or methyl;

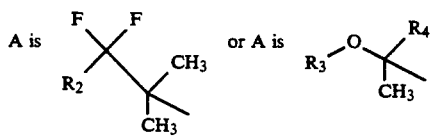

and $R_2$ is lower alkyl; $R_3$ is phenyl, or phenyl substituted by 1 to 3 substituents selected from the group consisting of halo, lower alkyl, and lower alkoxy; and $R_4$ is hydrogen or methyl; or a pharmaceutically acceptable salt of said acid, a $C_{1-4}$ alkyl ester of said acid, an acetylamino-substituted-$C_{1-4}$ alkyl ester of said acid, a phenyl-dimethylamino ester of said acid or a α-monoglyceride of said acid.

2. A composition for treating hyperproliferative skin diseases which comprises an antihyperproliferatively effective amount of a compound of the formula

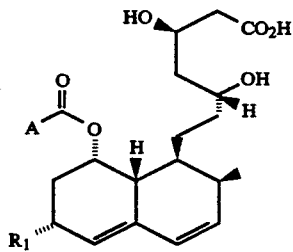

II wherein $R_1$ is hydrogen or methyl;

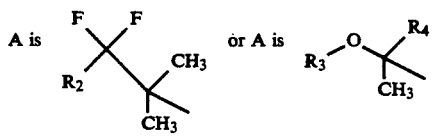

and $R_2$ is lower alkyl; and $R_3$ is phenyl, or phenyl substituted by 1 to 3 substituents selected from the group consisting of halo, lower alkyl, and lower alkoxy; and $R_4$ is hydrogen or methyl; or a pharmaceutically acceptable salt of said acid, a $C_{1-4}$ alkyl ester of said acid, an acetylamino-substituted-$C_{1-4}$ alkyl ester of said acid, a phenyl-dimethylamino ester of said acid or a α-monoglyceride of said acid; and a pharmaceutically acceptable carrier material.

3. A composition in accordance with claim 2 for oral administration.

4. A composition in accordance with claim 2, for topical administration.

5. A method for treating a hyperproliferative skin disease in a patient in need of such treatment comprising administering an antiproliferatively effective amount of a compound of formula

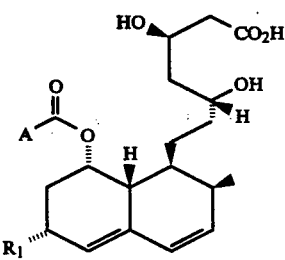

II wherein $R_1$ is hydrogen or methyl;

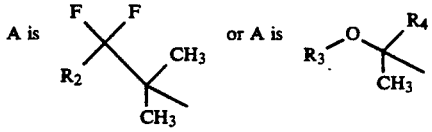

and $R_4$ is hydrogen or methyl; and $R_2$ is lower alkyl; and $R_3$ is phenyl, or phenyl substituted by 1 to 3 substituents selected from the group consisting of halo, lower alkyl, and lower alkoxy; or a pharmaceutically acceptable salt of said acid, a $C_{1-4}$ alkyl ester of said acid, an acetylamino-substituted-$C_{1-4}$ alkyl ester of said acid, a phenyl-dimethylamino ester of said acid or a α-monoglyceride of said acid.

6. A method in accordance with claim 5 wherein the compound of formula I is administered orally.

7. A method in accordance with claim 5 wherein the compound of formula I is administered topically.

8. A compound of the formula

IV wherein A is

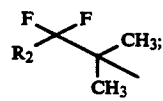

$R_2$ is lower alkyl; and X is chloro or bromo.

9. The compound in accordance with claim 23, 3,3-difluoro-2,2-dimethyl butanoic acid, or the acid chloride thereof.

10. A compound of the formula

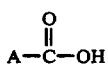

wherein A is

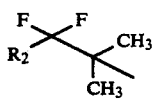

and R₂ is lower alkyl.

11. A method for lowering cholesterol which comprises administering an effective amount of a compound of the formula

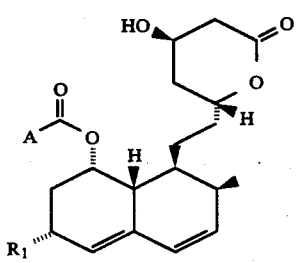

wherein R₁ is hydrogen or methyl;

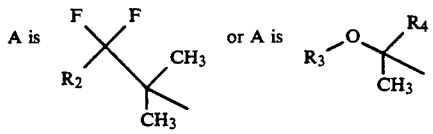

wherein R₂ is lower alkyl; R₃ is phenyl, or phenyl substituted by 1 to 3 substituents selected from the group consisting of halo, lower alkyl, and lower alkoxy; and R₄ is hydrogen or methyl.

12. A method in accordance with claim 11 wherein A is

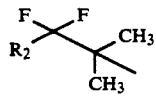

and R₂ is lower alkyl.

13. A method in accordance with claim 11 wherein the compound of formula I is 3,3-difluoro-2,2-dimethyl-butanoic acid, [1S-[1α,3β,7β,8β(2R*,4R*)8aβ]]-8-[2[tetrahydro-4-hydroxy-6-oxo-2H-pyran-2-yl]ethyl]-1,2,3,7,8,8a-hexahydro-3,7-dimethyl-1-naphthalenylester.

14. A method for lowering cholesterol which comprises administering an effective amount of a compound of the formula

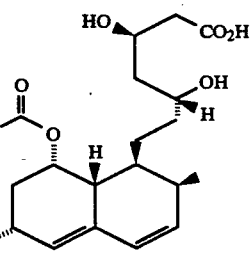

wherein R₁ is hydrogen or methyl;

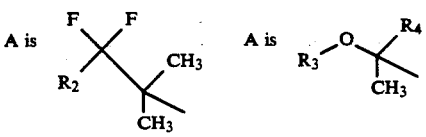

and R₂ is lower alkyl; R₃ is phenyl, or phenyl substituted by 1 to 3 substituents selected from the group consisting of halo, lower alkyl, and lower alkoxy; and R₄ is hydrogen or methyl; or a pharmaceutically acceptable salt of said acid, a C₁₋₄ alkyl ester of said acid, an acetylamino-substituted-C₁₋₄ alkyl ester of said acid, a phenyl-dimethylamino ester of said acid or a α-monoglyceride of said acid 15. A compound in accordance with claim 1 having the formula

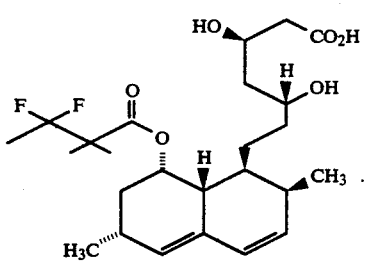

* * * * *

UNITED STATES PATENT AND TRADEMARK OFFICE
CERTIFICATE OF CORRECTION

PATENT NO. : 5,200,549
DATED : April 6, 1993
INVENTOR(S) : Ann Goldstein, John Arthur McLane, Peter Michael Wovkulich and Milan Radoje Uskokovic It is certified that error appears in the above-identified patent and that said Letters Patent is hereby corrected as shown below:

On the title page: Item

[73], please insert an -- n -- between the "a" and "n" of Hoffman.

In The Claims:

In claim 9, column 20, line 65, please change "claim 23" to -- claim 8 --.

In claim 14, column 22, line 36, add "." after the word "acid".

Signed and Sealed this

Seventh Day of December, 1993

Attest:

BRUCE LEHMAN

*Attesting Officer*     *Commissioner of Patents and Trademarks*